(12) United States Patent
Christiansen et al.

(10) Patent No.: US 10,426,474 B2
(45) Date of Patent: Oct. 1, 2019

(54) SUTURELESS DEVICE AND METHODS FOR CLOSING A TISSUE OPENING

(71) Applicant: Black Diamond Creations, LLC, St. George, UT (US)

(72) Inventors: Brett D Christiansen, Saint George, UT (US); Christopher B Christiansen, Saint George, UT (US); James B Christiansen, Saint George, UT (US); Clancy B Christiansen, Saint George, UT (US); Candice S Christiansen, Saint George, UT (US); Bryce B Christiansen, Saint George, UT (US); Susan G Christiansen, Saint George, UT (US); Phillip Dietz, Saint George, UT (US)

(73) Assignee: Black Diamond Creations, LLC, St. George, UT (US)

( * ) Notice: Subject to any disclaimer, the term of this patent is extended or adjusted under 35 U.S.C. 154(b) by 325 days.

(21) Appl. No.: 15/418,654

(22) Filed: Jan. 27, 2017

(65) Prior Publication Data

US 2018/0214148 A1    Aug. 2, 2018

(51) Int. Cl.
*A61B 17/08*    (2006.01)
(52) U.S. Cl.
CPC ...... *A61B 17/085* (2013.01); *A61B 2017/081* (2013.01); *A61B 2017/086* (2013.01)
(58) Field of Classification Search
CPC ... A61B 17/0466; A61B 17/08; A61B 17/083; A61B 17/085; A61B 17/8009; A61B 17/8019; A61B 90/02; A61B 2017/00407; A61B 2017/081; A61B 2017/086; A61B 2017/088

(Continued)

(56) References Cited

U.S. PATENT DOCUMENTS 3,926,193 A * 12/1975 Hasson ............... A61B 17/085
                                                    606/218
3,971,384 A    7/1976 Hasson (Continued)

FOREIGN PATENT DOCUMENTS

RU    2371117    10/2009
RU    171432    5/2017

OTHER PUBLICATIONS

Title: TopClosure® 3S System—Skin Stretching and Secure Wound Closure System URL: www.topclosure.com Date Captured: Nov. 11, 2015.

*Primary Examiner* — Katrina M Stransky
*Assistant Examiner* — Lindsey Bachman
(74) *Attorney, Agent, or Firm* — Gurr Brande & Spendlove, PLLC; Robert A. Gurr

(57) ABSTRACT

A sutureless device and methods for closing a tissue opening that minimizes the labor, cost, and skill typically required is disclosed. The apparatus comprises two anchors that attach to either side of an open tissue wound. The two anchors are connected together by a tie strip; the tie strip has a plurality of teeth and a rack. As the wound edges and anchors are brought together the ratchet system on the tie strip prevents the anchors and tissue wound from reopening. To control the distance between the two anchors, a rack and pinion system and a key or a lever system is utilized. The rack is located on the tie strip and the pinion is located on the key.

13 Claims, 11 Drawing Sheets

(58) Field of Classification Search
USPC .................................................. 606/214–218
See application file for complete search history.

(56) References Cited

U.S. PATENT DOCUMENTS

| | | |
|---|---|---|
| 4,815,468 A | 3/1989 | Annand |
| 5,879,291 A | 3/1999 | Kolata et al. |
| 2006/0009803 A1 | 1/2006 | Garay |
| 2006/0200198 A1 | 9/2006 | Riskin |
| 2013/0237895 A1* | 9/2013 | Rastegar ........... A61F 13/00021 602/53 |
| 2015/0223814 A1 | 8/2015 | Nash et al. |
| 2016/0235407 A1 | 8/2016 | Fox |

* cited by examiner

SUTURELESS DEVICE AND METHODS FOR CLOSING A TISSUE OPENING

BACKGROUND OF THE INVENTION

Field of the Invention

A sutureless device and method for closing a tissue opening that minimizes the labor, skill, and cost typically required to properly close tissue lacerations.

Background—Prior Art

One of the most common, costly and time-consuming activities that doctors perform is the suturing or closing of tissue wounds. Tissue wounds may be accidental or, a surgical incision and intentional. In addition to humans, animals also suffer from tissue wounds that require the skill of a veterinarian to close.

The basic concept of tissue wound closure is to bring the two wound edges mechanically together in close alignment, both vertically and horizontally. When the wound edges are properly aligned, the wound heals more quickly, scarring is lessened and infections are decreased. Although the concept of tissue wound closure is basic, the skills to properly close a tissue wound, using the current most common method of closure with sutures or tissue adhesive is done by a health care profession. It may take years to develop this skill. Access to health care providers is limited and often delayed requiring loss of time to get the repair done. In addition, the cost to get a wound repaired in the Emergency Department ranges anywhere from $500 up to $2,000.

When closing a tissue wound, a user must follow several precautions to prevent infections and scarring. Following proper irrigation and cleaning of the wound, the doctor's objective is to achieve the best wound edge approximation. This is the process of ensuring that the wound edges are brought together as evenly as possible during closing—both horizontally and vertically. If there is a gap between the two wound edges a dead space is created. This will lead to more scarring and a longer time required to heal. If the wound edges are too close, one of the edges of the wound may curl, causing misalignment, which is known as inversion. This may delay the healing process and may leave an unsightly scar.

The time period between the initial injury and the closure of the wound is also important. To lower the risk of infections it is essential that the wound be closed quickly. The longer the wound is left open, the more bacteria there is that enters the wound and begins to grow. Several studies have shown that a tissue wound is best closed within six hours or less. Many doctors refer to this six-hour period as the "golden period." Ideally a tissue wound should be closed within three hours. However, many times the patient is not near a medical facility or a doctor is not available for hours or even days. In addition, waiting times in Emergency Departments alone can be over 6 hours.

Previous wound closing methods included invasive and traumatizing methods such as sutures and staples. These methods required passing materials through the intact skin around the wound edges. These methods cause additional pain to the patient and increase the risk of infection. These methods, even if used by a skilled physician, may still cause pain and scarring caused by the sutures and staples themselves. It also requires expensive equipment and supplies that the general population do not have direct access to. To limit the pain, many doctors administer a local anesthetic. However, there are a number of adverse events that can occur from using these local anesthetics. These reasons are why such materials cannot be used by the general public and require a license and training. In addition to others, four of the most important are; First, the use of local anesthetics requires several needle punctures in the skin that increase the risk of infection and cause pain to the patient. Sometimes the process of providing local anesthetic causes as much pain as doing the repair by itself. Second, local anesthetic at times is inadvertently injected into a blood vessel running through the tissue, or into a nerve. This can cause significant adverse reactions. Third, some patients are allergic to local anesthetics. Finally, the use of needles increases the risk of diseases being accidently transmitted to the healthcare providers. What is need is a device that does not require local anesthetic or use of sutures, staples or puncture the skin in any way, the pain and risk of adverse reactions outlined above are minimized.

Several attempts to develop a sutureless device for wound closure have been developed in the past. One such example is the use of skin adhesives such as super glue (cyanoacrylates). However, these skin adhesives have several limitations. Even with appropriate training, they can be quite difficult and messy to use. The glue distributes itself due to gravity and pools in the lowest spot and not where you necessarily need it. Wound edges must be approximated perfectly before the glue is applied. This can be difficult to do while not gluing your fingers to the wound edges. Once applied, you cannot adjust or readjust the wound margins. You get vertical and horizontal misalignment causing increased scarring. Skin adhesives may only be used on small, clean lacerations and can therefore only be used on limited locations on the patient's body. Additionally, some patients are allergic to cyanoacrylates. The general public does not have access to this medical grade glue or have knowledge and skill of how to apply it appropriately. Cyanoacrylates that can be purchased at the store are not suitable or approved for wound closures. They do not have an elasticity component built into the glue and are brittle causing the glue to separate before it is appropriately healed and the wound opens up, causing increased scaring.

Other types of sutureless devices included strips of fabric or surgical tape. The wound is manually closed and the surgical tape is placed perpendicular to the tissue wound, preventing the wound from reopening. Like skin adhesives, surgical tape can only be applied to small, clean, shallow tissue wounds. These are not adjustable short of removing the entire bandage and replacing it. Removing the bandages may causes the wound to reopen again.

Several attempts have been made to develop a sutureless device for larger wounds. An early attempt to overcome these limitations is the device disclosed in the patent to Annand, U.S. Pat. No. 4,815,468. The embodiment disclosed in U.S. Pat. No. 4,815,468 utilized plates that attached to either side of the tissue wound. A mechanical element is attached to the plates and then the mechanical elements snapped the two plates together, thus pulling the skin together. The limitations to U.S. Pat. No. 4,815,468 are typical of many sutureless devices: the device fails to properly align the skin resulting in excess scarring. In addition, the device may only be utilized for smaller wounds.

Other sutureless devices are extremely complex, take an excessive amount of time to utilize or require special equipment. One such example is U.S. Pat. No. 8,197,506. In U.S. Pat. No. 8,197,506 a device is disclosed that requires the use of special forceps that includes the use of a locking mechanism to hold the tissue wound closed.

To overcome these limitations several devices were disclosed that did not require specialized equipment but nevertheless still provided the user only a limited ability to adjust the edges of the wound. In U.S. Pat. No. 3,926,193 a device is disclosed that consists of two anchors attached to the skin. Tie members connect the two anchors together. As the two anchors are brought together the gap between the two anchors decreases and therefore closes the tissue wound. However, U.S. Pat. No. 3,926,193 has several limitations. The device could only be utilized for linear tissue wounds, the device was unable to flex with the movement of the body, and the device lacked the ability for the user to properly adjust the skin alignment.

Another attempt is U.S. Pat. No. 3,971,334, which utilized tie strips connected to anchors on each side of the wound. As the anchors are squeezed the tie strips prevent the anchors from separating. While this was an improvement over the prior art, there are still several limitations to U.S. Pat. No. 3,971,334; in particular, it was still difficult for the user to properly adjust the distance between the anchors and properly align the skin.

What is needed is a sutureless device that can be used easily by untrained users or by the individual themselves. That will allow the user to properly align the skin, and that can flex with the movement of the body. In addition, the sutureless device should allow the user to use the device on jagged tissue wounds or contoured or rounded body parts. The design and materials of this device will allow it to be manufactured in high volumes that allows it to be affordable and available to the general public. It will also not require the user to have special equipment, local anesthetic, or training in order to effectively use the product.

SUMMARY

A principal object of the invention is to provide a sutureless device for easily closing an open tissue wound. There are three main objects of the invention. First, the invention easily closes an open tissue laceration, and to produce a device in such a way that it is easily accessible to all, including healthcare providers, veterinarians, and especially the general public. Second, the invention decreases the pain, infection and scarring associated with wound repair. Third, the invention significantly decreases the cost and inconvenience required to repair wounds that are found to be appropriate for closure by the device.

As part of the object of the invention is to provide a device that allows the user to delicately close the tissue wound by properly aligning the two skin edges of the tissue wound both horizontally and vertically. The device has flexible and expandable connections between each individual device to allow for irregular wounds or complex skin contour as well as the ability to flex with the movement of the body and adjust to the contour of the body. Still another object of the invention is to provide a device that can be easily adjusted or readjusted for uneven or jagged tissue wounds. In addition, the device will enable the individual to fine-tune the exact alignment of the wound for the best possible result in wound closure and decrease in scarring. Another object the device is to allow it to be used as a single unit for a small laceration or as a group of attached units to close a larger or irregularly shaped laceration. Provide devices to the general public, such that the general public is able to immediately apply the device themselves, thus not only significantly decreasing cost, but significantly decreasing the time required to get the wound closed, which will decrease the bacterial load and chance of wound infection.

The present invention comprises two anchors that attach to opposing sides of an open tissue laceration. The two anchors are connected together by means of a tie strip. As the two edges of the tissue wound are drawn together, the two anchors are brought together. The tie strip ratcheting system prevents the anchors from separating and thus prevents the tissue wound from reopening.

To control the distance between the two anchors, a rack and pinion system is utilized. The rack is located on the tie strip, and the pinion is located on a key. To assist the user in utilizing the key, a raised boss is located on one of the anchors that corresponds to an orifice on the bottom of the key. In the alternative, the device may utilize a lever to control the distance between the two anchors.

As the user turns the key, the rack and pinion system converts the rotational motion of the key to the linear motion of the tie strip. The movement of the tie strip causes the two anchors to come together and therefore closes the open wound. The tie strip ratchet system prevents the anchor and the wound from reopening. There is a release latch that can be lifted allowing the ratchet to be temporarily released such that you can adjust for potential over tightening, enabling you get the best possible wound closure. In the alternative, a lever may be used to control the movement. In addition, an optional lock may be utilized to prevent the movement of the tie strip.

DESCRIPTION OF THE DRAWINGS

The invention may take form in certain parts and arrangement of parts, and preferred embodiment of which will be described in detail in the specification and illustrated in the accompanying drawing, which for a part hereof.

Figure 1:
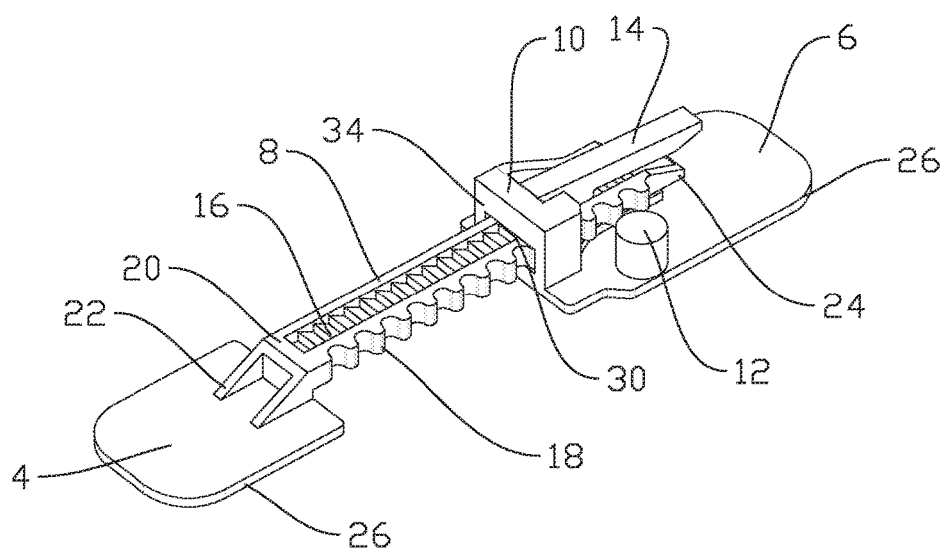
FIG. 1 shows an elevated side plan view of the tissue closing device of the invention.
Figure 2:
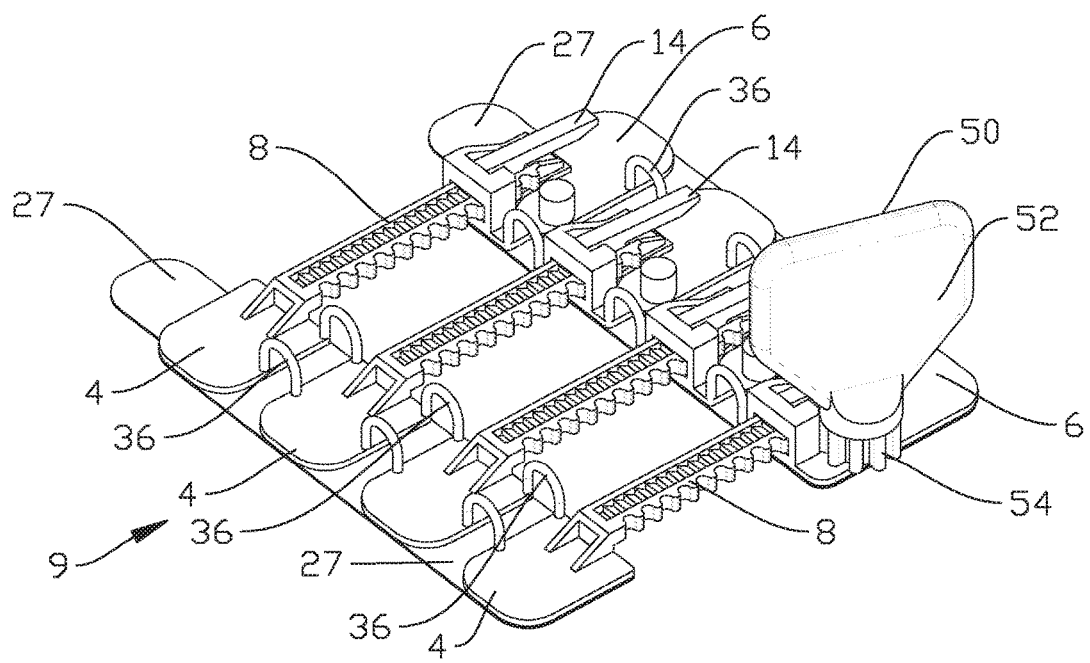
FIG. 2 shows an array of the tissue closing device, illustrating how each tissue closing device is connected to the other tissue closing devices; in addition shows a key releasably connected to one of the tissue closing devices in the array.

| Drawing Reference Numbers | |
|---|---|
| 2 | Tissue closing device |
| 4 | Anchor base |
| 6 | Receiving base |
| 8 | Tie strap |
| 9 | Array |
| 10 | Receiving body |
| 12 | boss |
| 14 | Latch |
| 15 | Pawl |
| 16 | Teeth |
| 18 | Rack |
| 20 | starting end |
| 22 | Anchor buttress |
| 24 | Tip |
| 25 | Recess |
| 26 | pad |
| 27 | Adhesive cover |
| 28 | Adhesive |
| 29 | Cover tab |
| 30 | Slide port |
| 32 | Cross member |
| 34 | Side |
| 36 | Coupler |
| 38 | Scissors |
| 50 | Key |
| 52 | Handle |
| 54 | Pinion |
| 56 | Orifice |
| 58 | Shaft |
| 60 | Lock |
| 62 | Lock hook |
| 64 | Catch |
| 70 | Lever |
| 72 | pivot point |
| 74 | Lever clasp |

| Drawing Reference Numbers | |
|---|---|
| 76 | Lever mortise |
| 100 | Tissue wound |
| 102 | Skin |
| 104 | Bandage |

DESCRIPTION

The following discussion describes embodiments of the invention and several variations of these embodiments. This discussion should not be construed, however, as limiting the invention to these particular embodiments. Practitioners skilled in the art will recognize numerous other embodiments as well. It is not necessary that the device have all the features described below with regard to the specific embodiment of the invention shown in the figures.

In the following description of the invention, certain terminology is used for the purpose of reference only and is not intended to be limiting. Terms such as "upper," "lower," "above," and "below" refer to directions in the drawings to which reference is made. Terms such as "inward" and "outward" refer to directions toward and away from, respectively, the geometric center of the component described. Terms such as "side," "top," "bottom," "horizontal," and "vertical" describe the orientation of portions of the component within a consistent but arbitrary frame of reference which is made clear by reference to the text and the associated drawings describing the component under discussion. Such terminology includes words specifically mentioned above, derivatives thereof, and words of similar import.

Referring generally to FIGS. 1 through 22, a tissue closing device 2 comprising of an anchor base 4, a receiving base 6, and a tie strap 8 for closing a tissue wound 100. As shown in FIGS. 3, 7, 9, and 10, a key 50 comprising of a handle 52 and pinion 54. Another embodiment of the invention is shown in FIGS. 17, 18, 19 and 20 comprising the use of a lever 70. Each item will be discussed in detail below.

Figure 3:
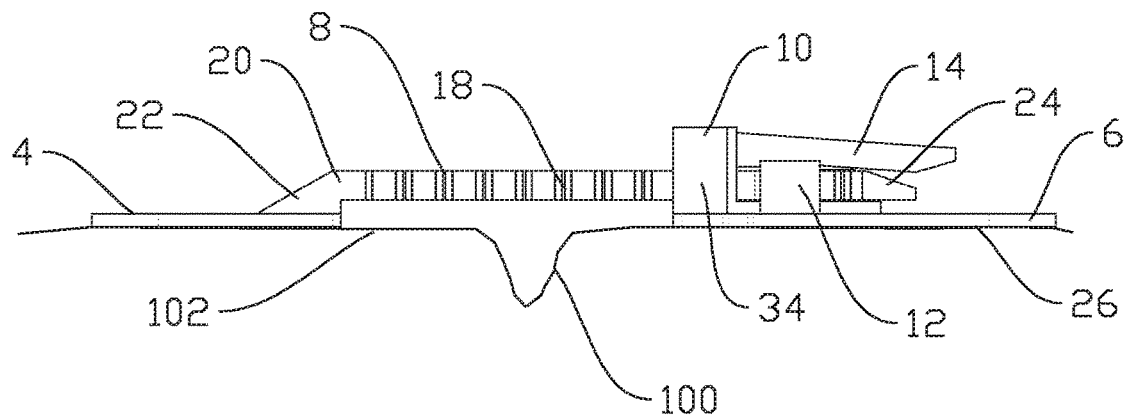
FIG. 3 shows a side view of the tissue closing device that shows the device attached to a user's skin and a tie strip bridging over an open tissue wound.
Figure 4:
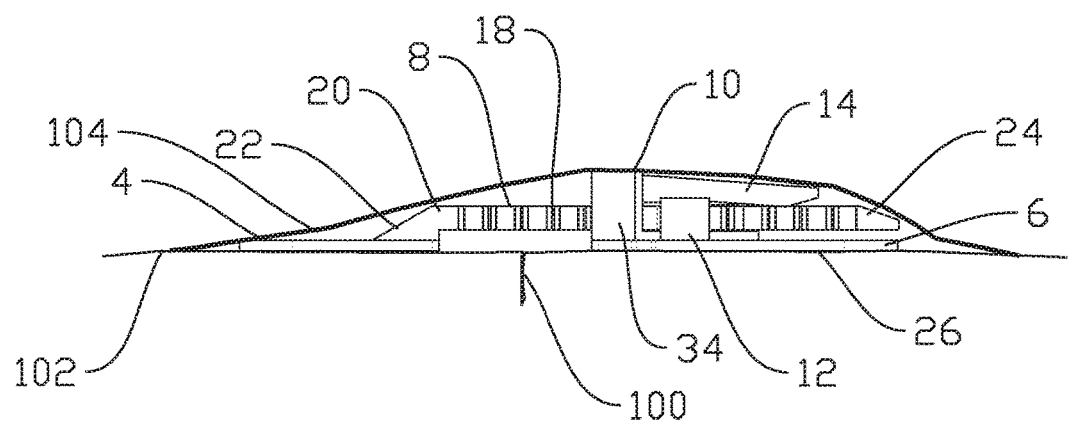
FIG. 4 shows a side view of the tissue closing device that shows the device attached to a user's skin and a tie strip bridging over the tissue wound with the tissue wound closed and the wound's edges properly aligned; in addition, shows a badged covering the device and the tissue wound.
Figure 22:
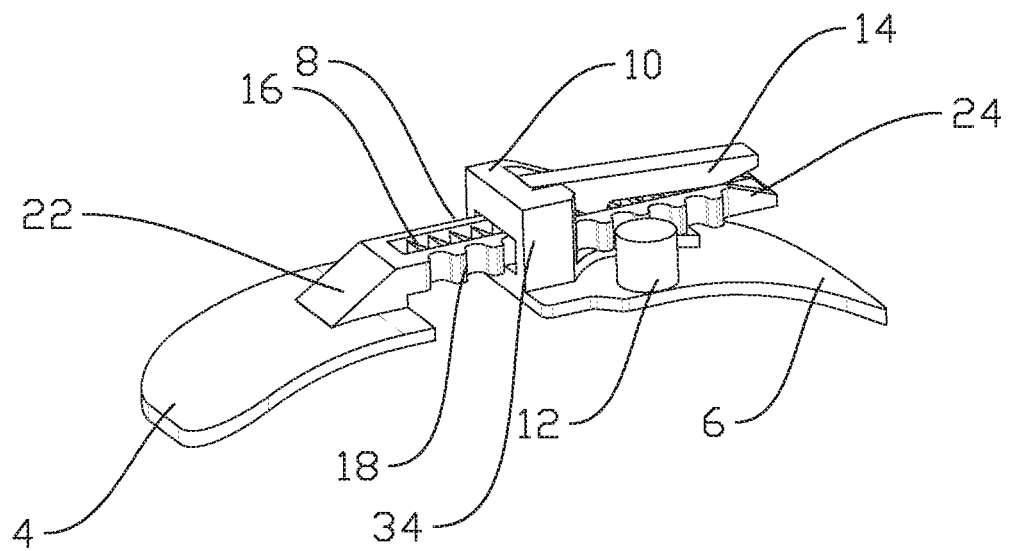
FIG. 22 shows an elevated side view of the device that is formed in a shape arc to match the contours of the body, such as a finger.

As illustrated in FIGS. 3 and 4, the anchor base 4 and the receiving base 6 attach to a patient's skin 102. The anchor base 4 is attached near the edge of a tissue wound 100. The receiving base 6 is attached on the opposite side near the edge of the tissue wound 100. The anchor base 4 and the receiving base 6 is preferably composed of a semi-rigid material such as nylon or plastic; however, flexible materials, metals or any semi-rigid materials are suitable for use in the present invention. The width and length of the anchor base 4 and the receiving base 6 vary based upon the size of the tissue wound 100. Larger tissue wounds 100 will require a larger sized anchor base 4 and receiving base 6. In application, a user would have a variety of different sizes available, and the user would select the appropriate size tissue closing device 2 determined by the size of the tissue wound 100. In addition, as shown in FIG. 22, the tissue closing device 2 may be curve or arc to confirm with the shape of the body, such as a finger or chin. The specific shape of the anchor base 4 and the receiving base 6 may also vary.

Located on the bottom of the anchor base 4 and the receiving base 6 is an adhesive 28. The adhesive 28 is for attaching the anchor base 4 and the receiving base 6 to the patient's skin 102. The adhesive 28 is generally any hydrophilic adhesive or medical adhesive agent such as a hydrocolloid, a hydrogel, or an acrylic polymer. However, many different types of adhesives 28 may work and are well known in the profession. As one skilled in the art will recognize, if the size of the anchor base 4 and the receiving base 6 increases, the surface area of the adhesive 28 increases, thus increasing the strength of the connection between the skin 102 and the anchor base 4 or receiving base 6.

To increase the comfort of the patient, a pad 26 may be placed between the adhesive 28 and the bottom of the anchor base 4 or the receiving base 6. The pad 26 may be installed in a recess 25 located on the base of the anchor base 4 and the receiving base 6. The shape and depth of the recess 25 is similar to the pad 26. The pad 26 will typically be flexible and more elastic than the anchor base 4 and the receiving base 6. The flexibility of the pad 26 will help maintain adhesion, minimize blister, and reduce irritation as well as adapts to irregularities of the surface of the skin 102.

Figure 5:
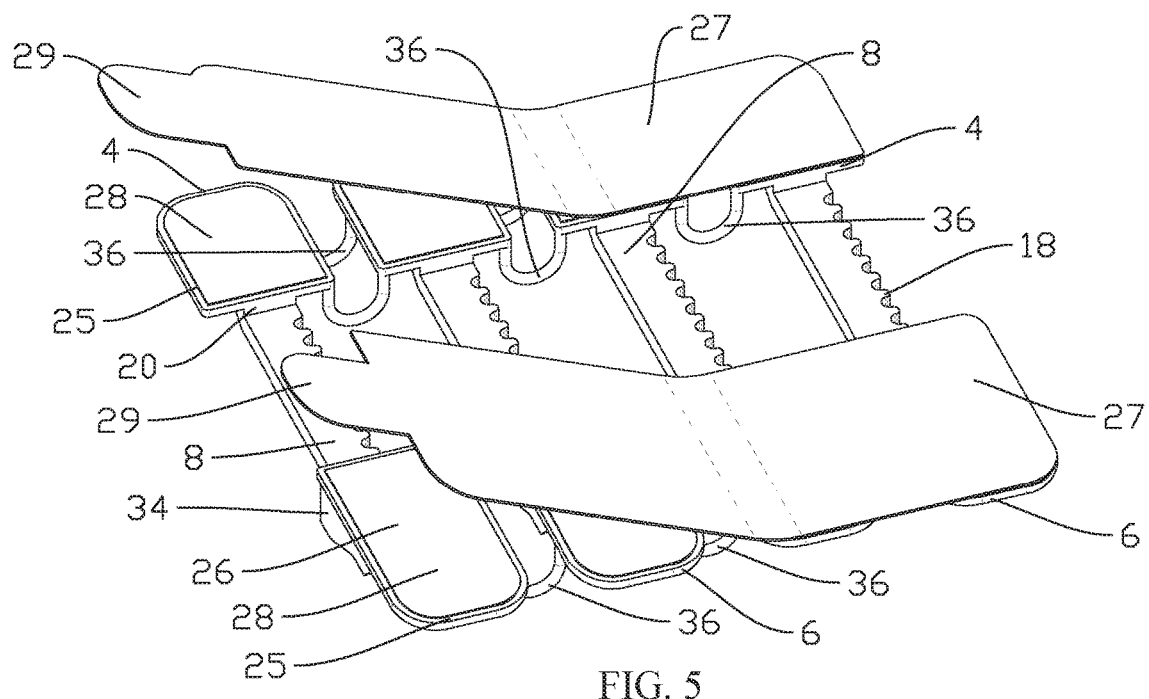
FIG. 5 shows a bottom view of an array of the tissue closing device; showing the locations of the adhesive pads and an adhesive cover.

As seen in FIG. 5, an adhesive cover 27 protects the adhesive 28. In addition, the adhesive cover 27 helps keep the adhesive 28 free of bacteria or viruses. The adhesive cover 27 is a protective layer that may be peeled away immediately prior to use. Generally, the adhesive cover 27 is coated paper but may be made of plastic or any other suitable material. The adhesive cover 27 must be easily removable by the user. In application, many users will use protective gloves to assist them in obtaining a stronger grip on the adhesive cover 27. A tab 29 is located on the edge of the adhesive cover 27. The tab 29 is generally made of the same material as the adhesive cover 27.

As illustrated in FIGS. 3 and 4, the tie strap 8 connects the receiving base 6 and the anchor base 4 by bridging over the tissue wound 100. The tie strap 8 comprises a starting end 20, a tip 24, a rack 18, and a plurality of teeth 16. Generally, the tie strap 8 is comprised of the same material as the anchor base 4 and the receiving base 6. The starting end 20 is attached to the anchor base 4. To increase the strength of the connection between the starting end 20 and the anchor base 4, additional anchor buttresses 22 may be added. In the preferred embodiment, the tie strap 8, anchor buttress 22, and the anchor base 4 are integrally formed from the same material. Located at the opposite end of the longitudinal axis of the tie strip 8 is the tip 24. The tip 24 has a spearhead shape to allow the user to easily insert the tie strap 8 into a receiving body 10. The tie strap 8 length, width and thickness vary based upon the size of the tissue wound 100 and the actual need. However, the size of the tie strap 8 must be able to withstand a tension force to prevent the tissue wound 100 from reopening.

Figure 15:
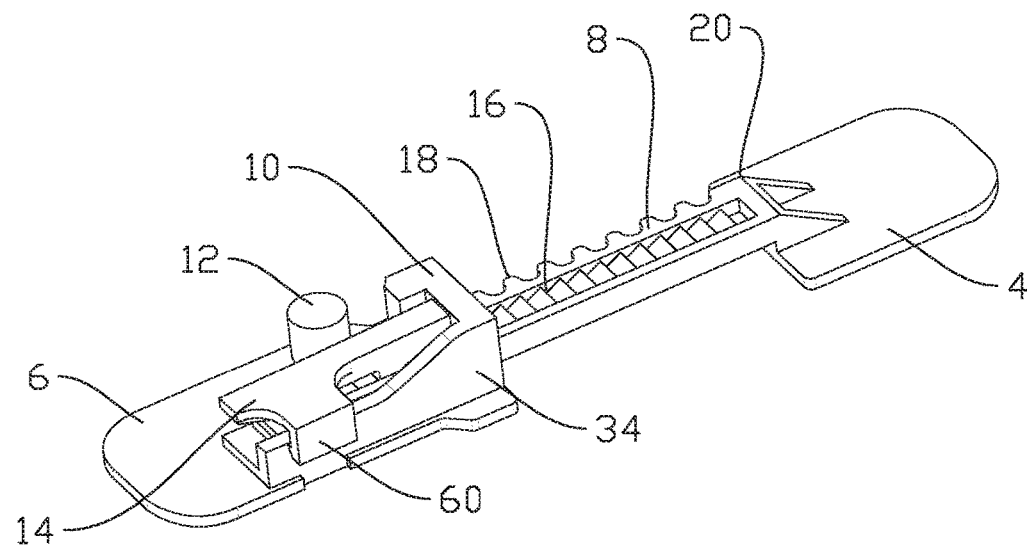
FIG. 15 illustrates an elevated side view of the device that includes a lock that prevents movement of the tie strip.

Located on the top of the tie strap 8 are the teeth 16. The teeth 16 are axially spaced along the longitudinal axis of the tie strap 8 for engaging with a pawl 15, which is described below. Located on the side of the tie strap 8 is the rack 18. The rack 18 is essentially an axially spaced gear bar that engages with the pinion 54 or lever 70 as illustrated in FIG. 15 or any other mechanical device which will incrementally close the distance between receiving base 6 and anchor base 4. located on the key 50. As one skilled in the art will recognize, the location of the rack 18 and the teeth 16 may be located on any side of the tie strap 8.

Figure 8:
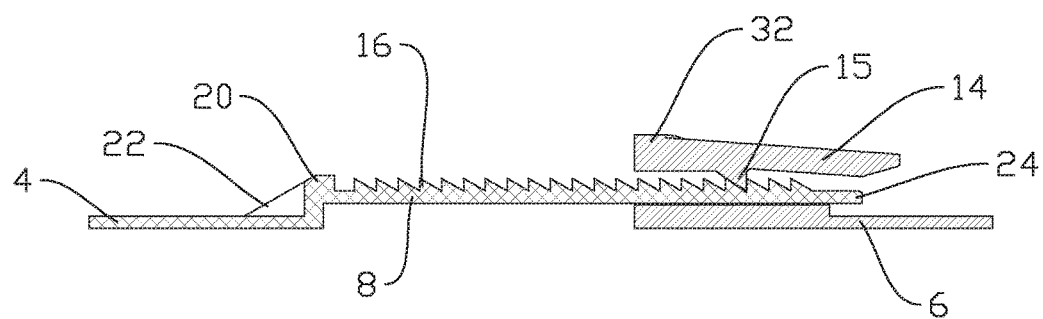
FIG. 8. shows a cross section view of the tissue closing device, showing how the teeth located on a tie strap interacts with a latch and a pawl.
Figure 9:
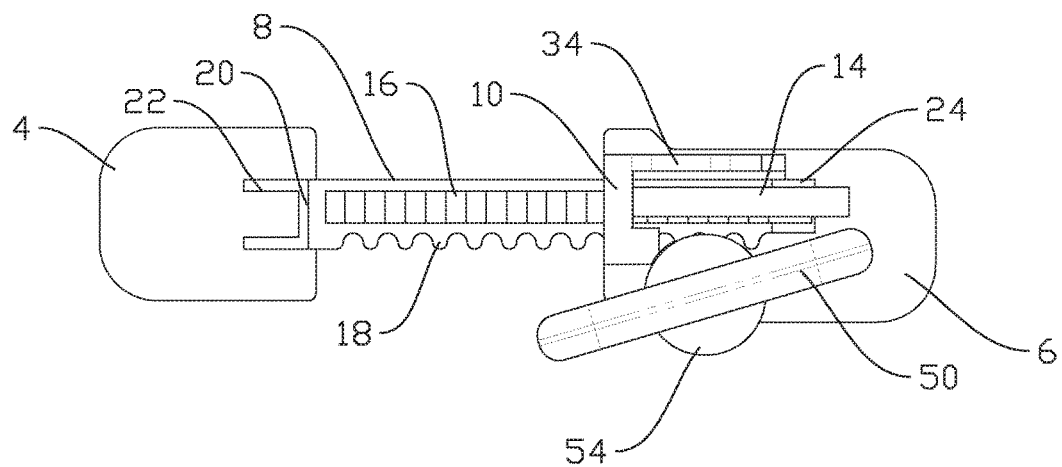
FIG. 9. shows a top view of the device with the key placed on the receiving anchor.

FIG. 8 is an illustration of the receiving body 10 that is located on the receiving base 6. The receiving body 10 includes a slide port 30, a cross member 32, two slides 34, and a latch 14. The slide port 30 is an opening for reception of the tie strap 8. The size of the slide port 30 is slightly larger than the size of the tie strap 8, such that the tie strap 8 will easily glide into the slide port 30 but small enough to prevent the tie strap 8 from freely moving. Generally, the receiving body 10 is integrally formed on the receiving base 6.

As shown in FIG. 8, a latch 14 is pivotally connected to the receiving body 10. However, the connection only allows the latch 14 to move when a force is applied to it. The latch 14 includes the pawl 15 that extends from the latch 14 into the slide port 30. As the tie strap 8 is passed through the slide port 30, the slope of the teeth 16 push the pawl 15 away from the tie strap 8, allowing the tie strap 8 to slide further into the receiving body 10. When tension is applied to the tie strap 8 to withdraw it from the receiving body 10, the latch 14 acts to position the pawl 15 so that the pawl 15 firmly grips one of the teeth 16. Thus the pawl 15 only allows the tie strap 8 to move in one direction. If the user wishes to withdraw the strap 8 from the receiving body 10, the user must intentionally lift the latch 14 so that the pawl 15 is raised above the teeth 16.

Figure 16:
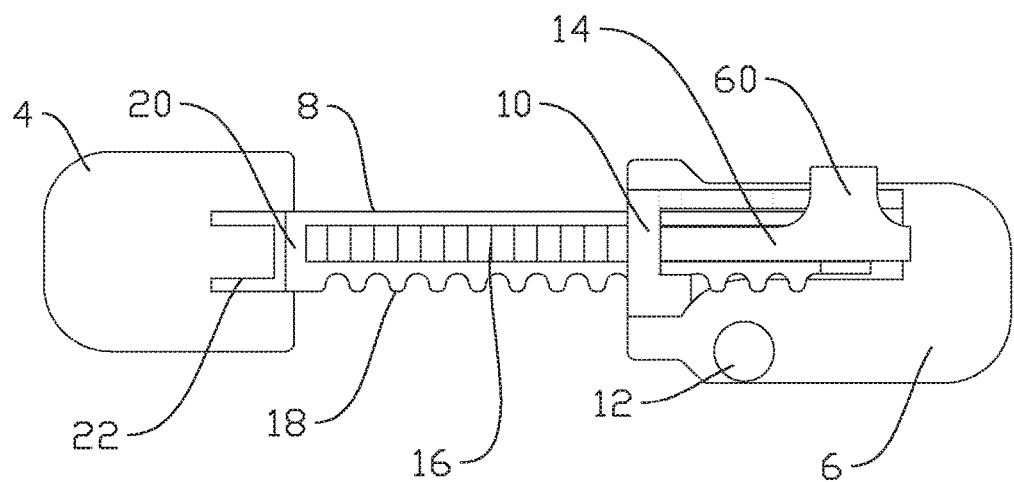
FIG. 16 shows a top view of the device with the lock that prevents movement of the tie strip.
Figure 17:
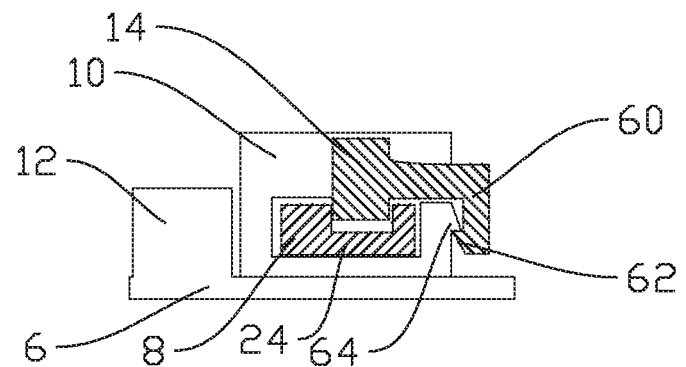
FIG. 17 shows a side view of the device with the lock in a closed position, therefore would prevent movement of the tie strip.
Figure 18:
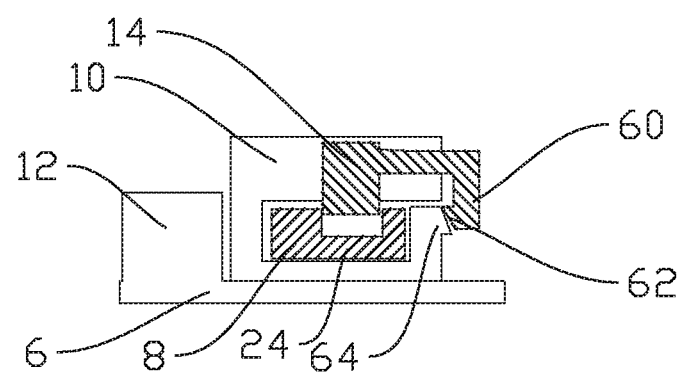
FIG. 18 shows a side view of the device with the lock in an open position, therefore allowing movement of the tie strip.

As illustrated in FIGS. 15 and 16, a lock 60 is located on the latch 14. The lock 60 prevents the movement of the tie strap 8 in any direction. The lock 60 extends down from the latch 14 parallel to the sides 34. Located at the end of the lock 60 is a lock hook 62. Located on the sides 34 is a catch 64. To prevent movement of the tie strap 8, the user pushes the latch 14 towards the receiving base 6. The movement of the latch 14 lowers the pawl 15 towards the teeth 16 so that the pawl 15 creates an interference fit with one of the teeth 16 and prevents movement of the tie strap 8. To prevent the latch 14 from returning to it normal location, the lock hook 62 engages with the catch 64 as shown in FIG. 17.

As described above and shown in FIGS. 3 and 12, the key 50 is releasably connected to the anchor base 4. The key 50 comprises the handle 52 and the pinion 54. The handle 52 is of a size that allows the user to easily grip it and apply a rotational force to the key 50. The handle 52 may have several different shapes and sizes. Located at the base of the key 50 is the pinion 54. The pinion 54 generally has a gear-like shape and corresponds with the rack 18 located on the tie strap 8. A shaft 58 is positioned between the pinion 54 and the handle 52 to raise the handle 52 above the receiving base 6. The key 50 is made of any semi-rigid or rigid materials such as nylon, plastic or metal. However, other suitable materials may also be utilized such as metals.

Located at the base of the key 50 and in the center of the pinion 54 is an orifice 56. Located on the receiving base 6 is a boss 12. Generally, the boss 12 has a circular shape. The orifice 56 has a size and shape slightly larger than the boss 12, such that the user may place the orifice 56 over the boss 12, creating a tight fit, yet allow the user to freely turn the key 50. One skilled in the art will acknowledge that there are several embodiments for releasably connecting the key 50 to the receiving base 6. One such embodiment is the receiving base 6 have a recessed well in order to receive the key 50.

Figure 19:
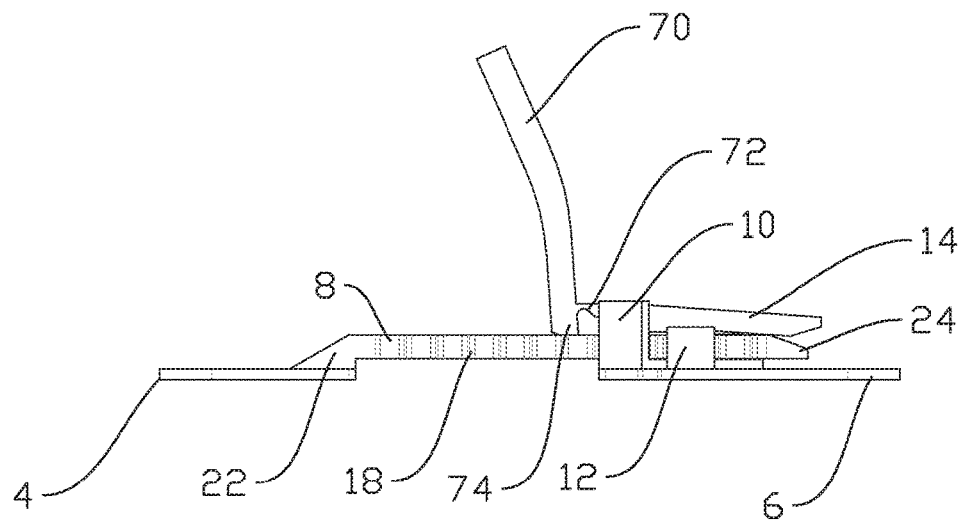
FIG. 19 shows a side view of the device with a lever; the lever being integrally formed with the receiving base.
Figure 20:
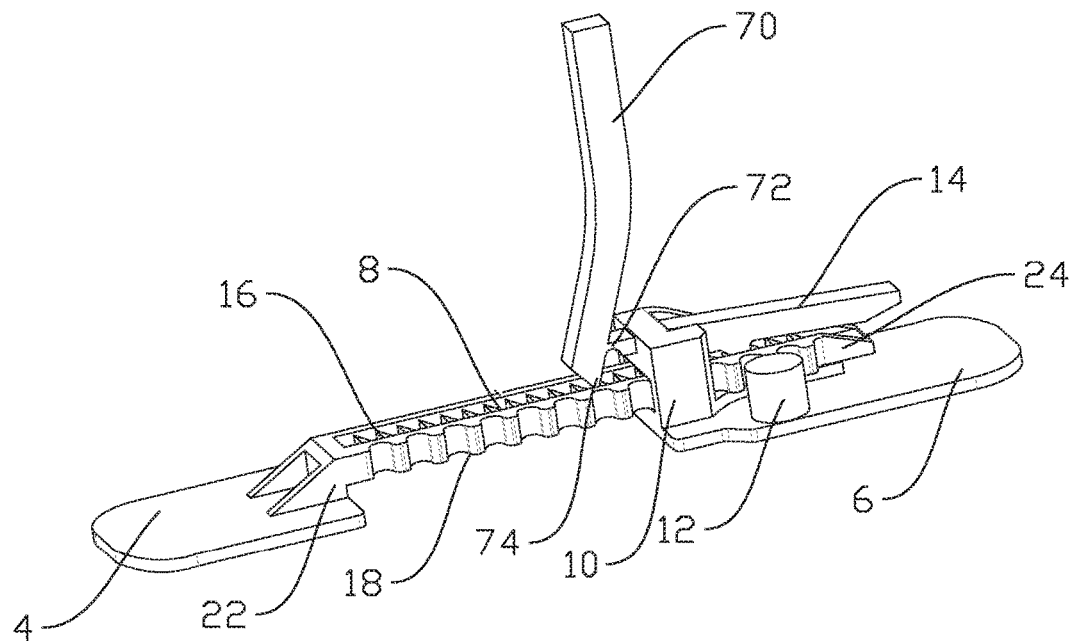
FIG. 20 shows an elevated side view of the device with a lever that is integrally formed with receiving base.
Figure 21:
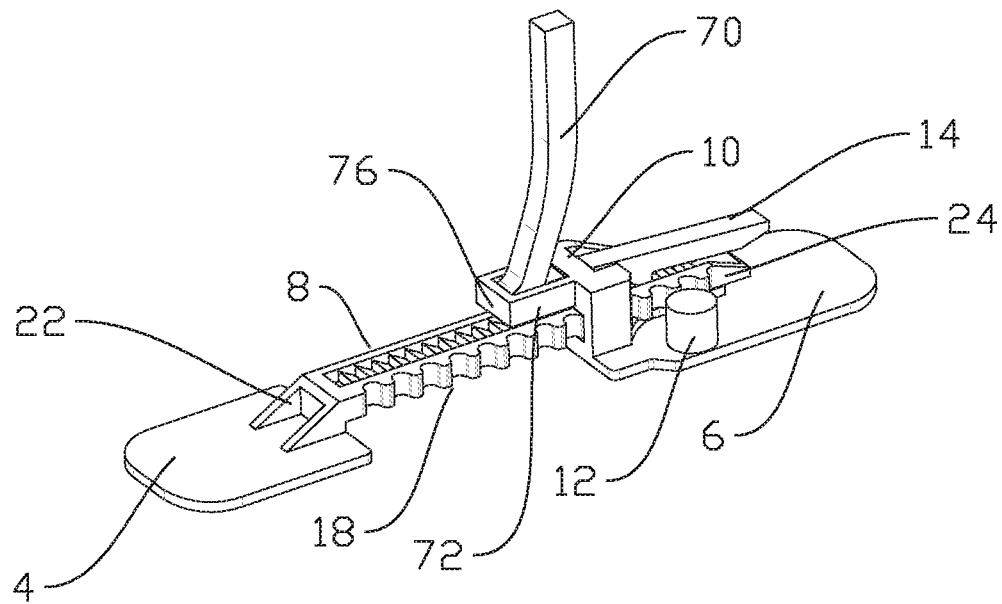
FIG. 21 shows an elevated side view of the device with a removable lever.

One embodiment of the invention is illustrated in FIGS. 19 and 20, which utilizes a lever 70. The lever 70 releasably connects to and engages receiving body 10. Located at the base of the lever 70 is a lever clasp 74. The lever clasp 74 extends towards the tie strip 8 and the teeth 16. The lever 70 acts as a ratchet, advancing the tie strap 8 forward with precise control. When the users actuates the lever 70, the lever 70 pivots at the pivot point 72 and causes the lever clasp 74 to move. The lever clasp 74 engages with one of the teeth 16 and pushes the tie strap 8 and the anchor base 4 towards the receiving base 6. When the tissue wound 100 is closed, the lever 70 is removed or positioned parallel to the body of the tie strap 8 to prevent interference with a bandage 104. FIGS. 19 and 20 shows the lever 70 integrally formed with the receiving base 6. However, FIG. 21 shows an alternative way for the lever 70 attaching to the receiving base 6 by utilizing a Lever mortise 76. One who is skilled in the art would recognize that there are several methods of creating pivot point 72 and creating a method for advancing tie strap 8.

Figure 6:
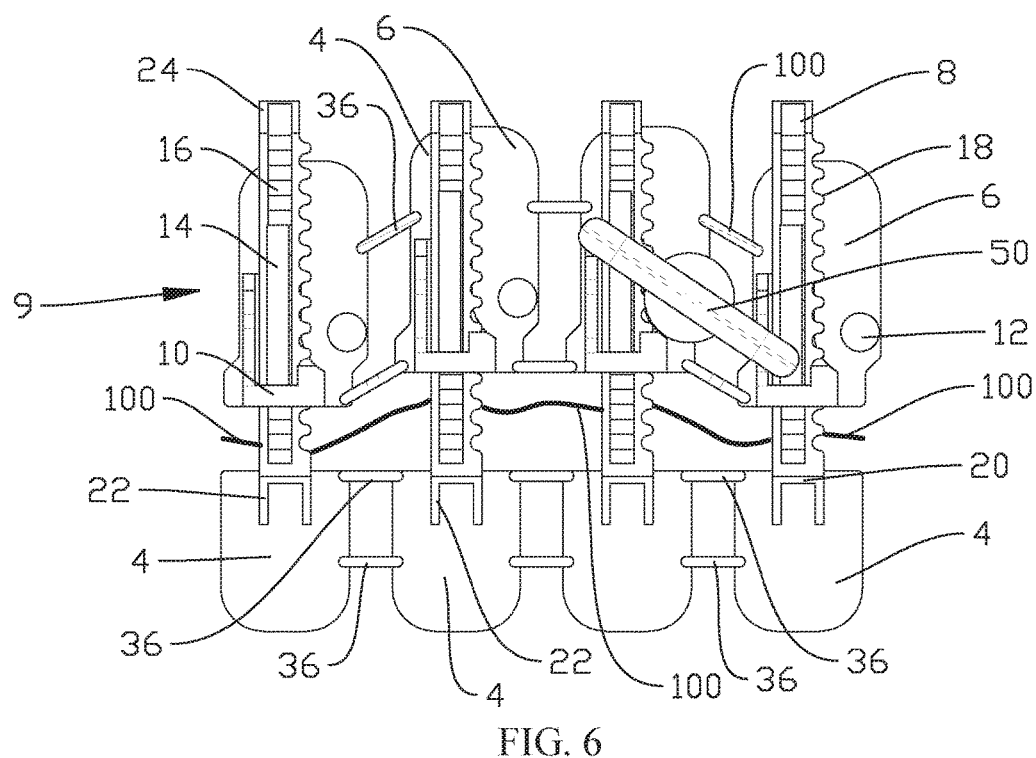
FIG. 6 shows a top view of an array of tissue closing devices, illustrating how the location of each tissue closing device may vary based upon the type and location of the tissue wound.
Figure 7:
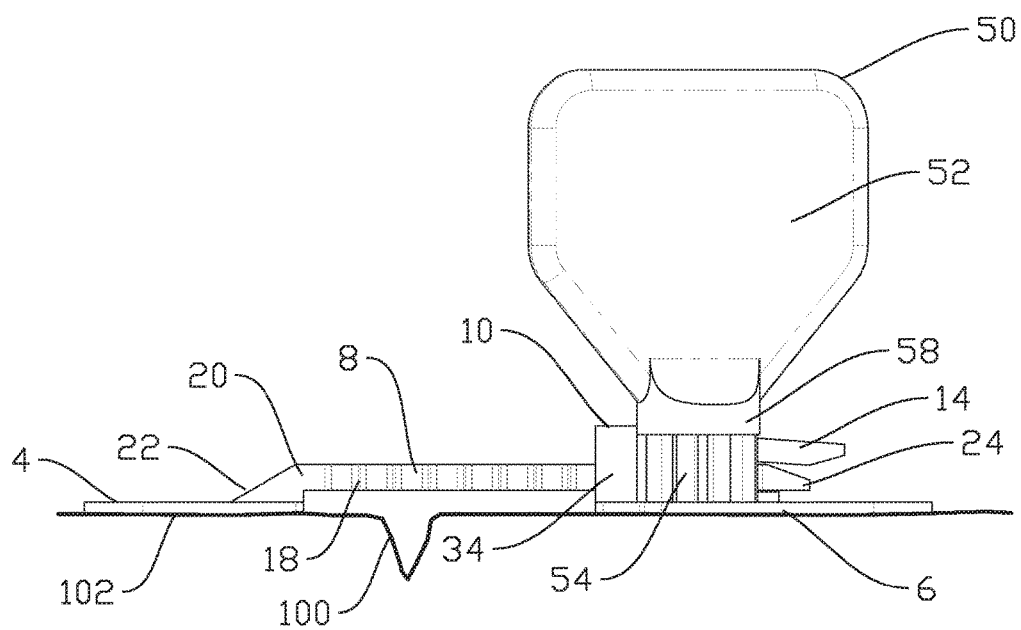
FIG. 7 shows a side view of the tissue closing device with an open wound showing how the tissue closing device bridges over an open wound, also illustrating how a key is position onto receiving base.
Figure 10:
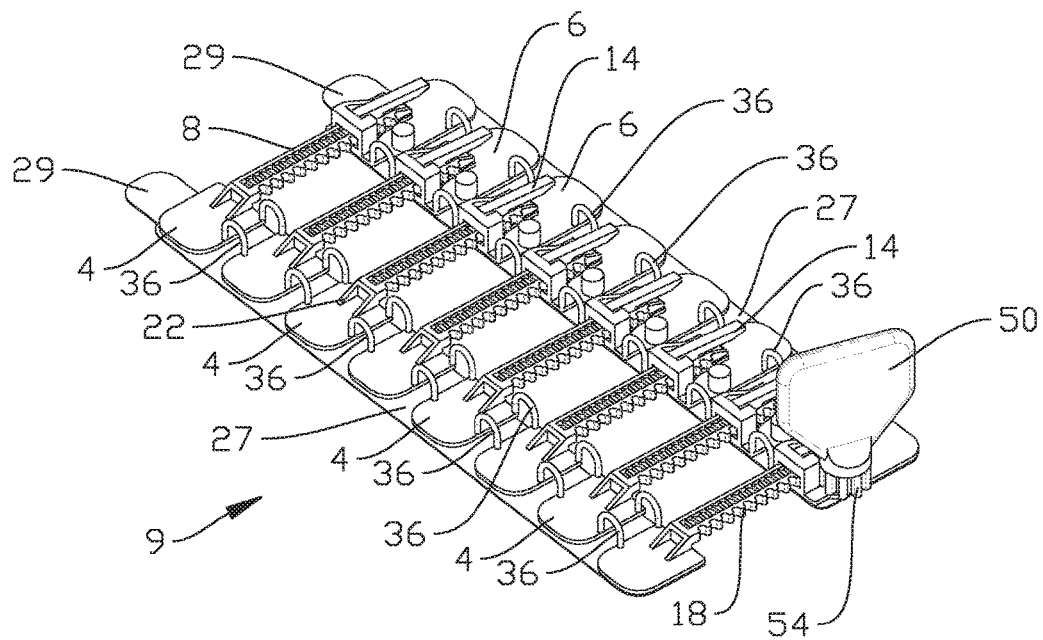
FIG. 10 shows an elevated side view of an array of tissue closing devices and the key; illustrating variable number of tissue closing devices that may be combined in the array.
Figure 11:
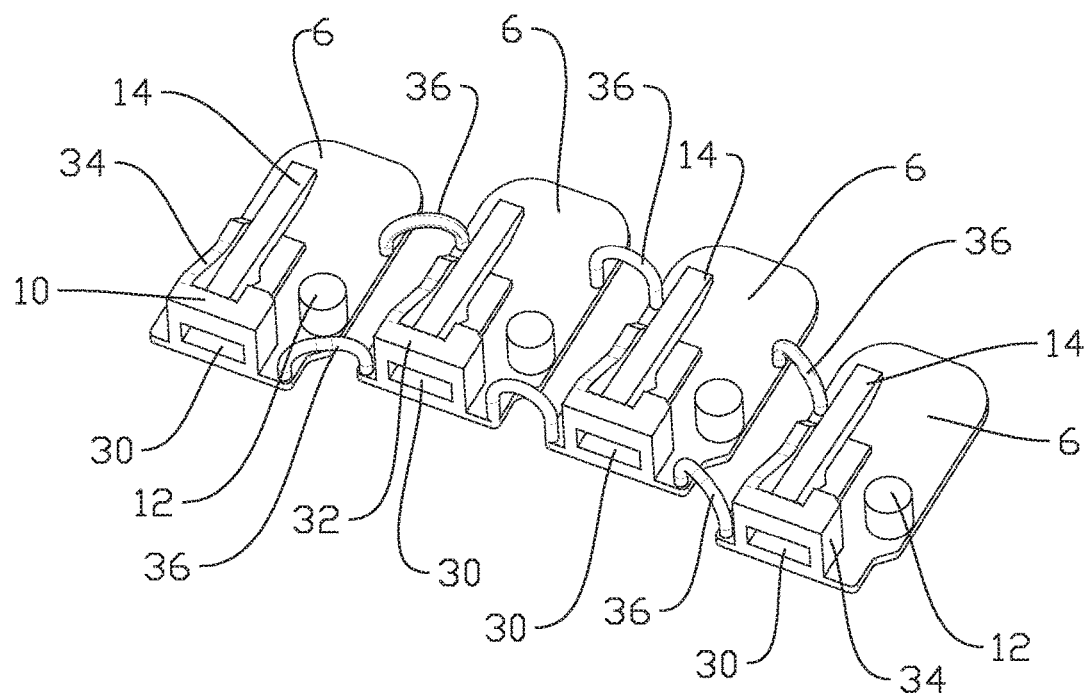
FIG. 11 shows an elevated side view of an array of the receiving anchors, illustrating the connection between each device is flexible and the array may be adjustable for jagged wounds or adjust to the contour of the body.
Figure 12:
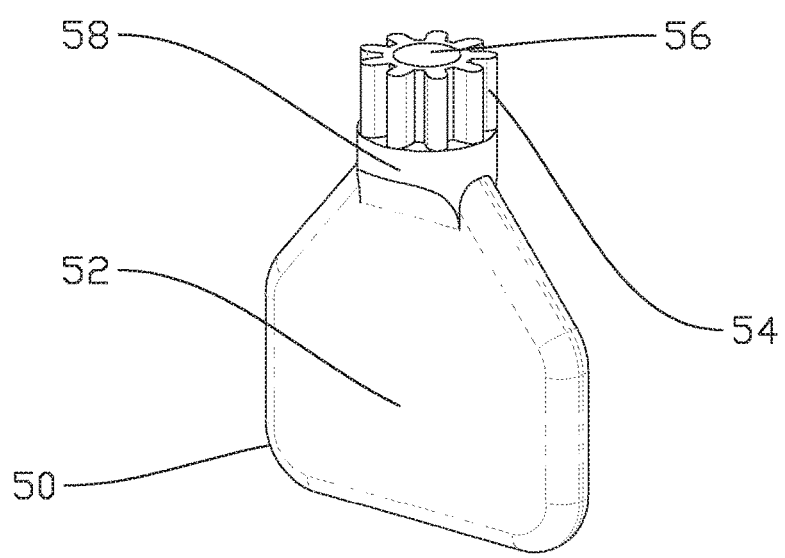
FIG. 12 shows the a bottom view of the key.
Figure 13:
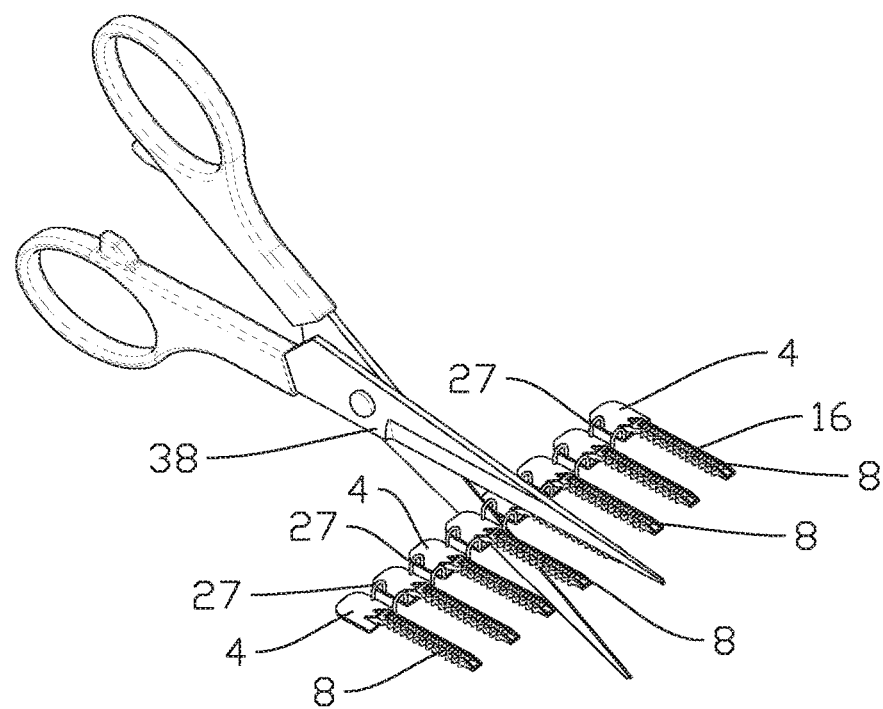
FIG. 13 shows an array of the tissue closing devices, illustrating how a user may utilize a cutting device such as scissors to separate the tissue closing devices.
Figure 14:
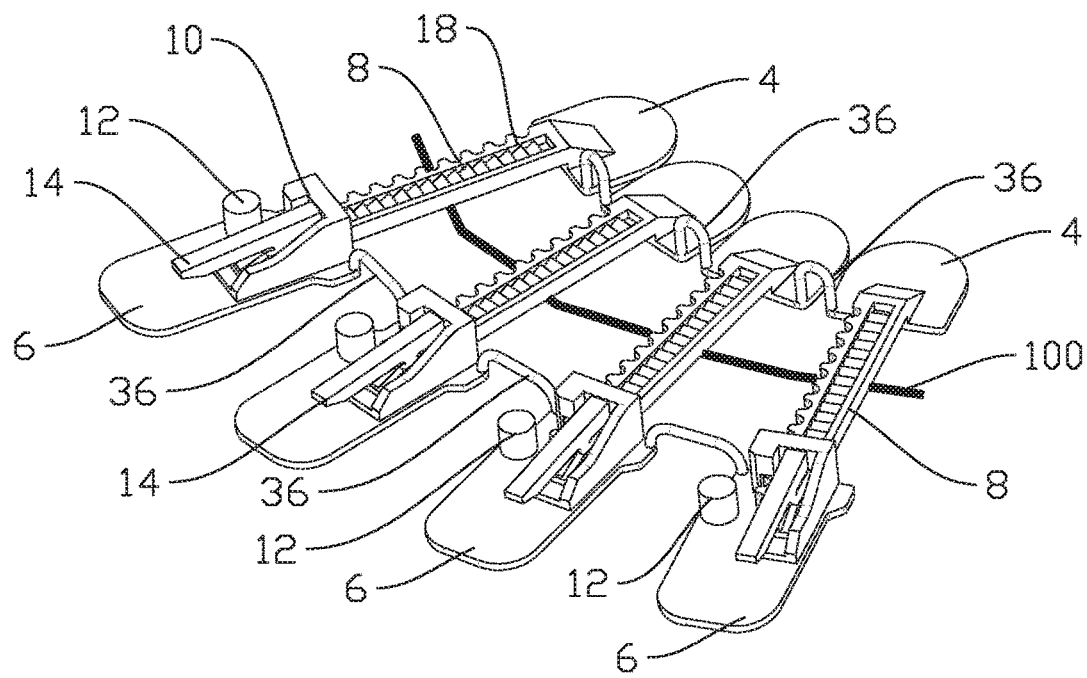
FIG. 14 shows an elevated side view of an array of the devices, illustrating the connection between each device is flexible and the array may be adjustable for arced tissue wounds or adjust to the contour of the body.

As illustrated in FIGS. 3, 4, and 10, a coupler 36 may connect several tissue closing devices 2 together in an array 9. The coupler 36 may connect to either or both the anchor base 4 and the receiving base 6. While FIGS. 3, 4, and 10 show four couplers 36 connecting each tissue closing device 2, different multiples of couplers 36 may be utilized. The coupler 36 may be made from any flexible or semi-flexible material such as nylon. The flexibility, compressability or expandability of the coupler 36 allows the user to adjust the location of each tissue closing device 2. As illustrated in FIG. 6, the coupler 36 is easily severed. However, in some embodiments, the coupler 36 is rigid and resilient.

In practice, an array 9 of tissue closing devices 2 are supplied to the user. The user determines the number of tissue closing devices 2 required to properly close the tissue wound 100 and removes the excess tissue closing devices 2 from the array 9. FIG. 4 shows a pair of scissors 38 or other cutting devices needed to separate the tissue closing device 2. If the tissue wound 100 is extremely jagged or located on a curved or rounded portion of the body, the user may separate all the tissue closing devices 2. Preferably, the longitudinal axis of each tissue closing device 2 is perpendicular to the longitudinal axis of the tissue wound 100 at a particular point on the tissue wound.

As shown in FIG. 4, a thin film bandage 104 is position over the entire device 2 and wound 100. Typically, the bandage 104 is a transparent film, but could be opaque and of various different materials. The bandage 104 is to protect the wound 100 from bacteria and debris. In addition, the bandage 104 prevents the device 2 from being snagged on outside objects. Furthermore, the bandage 104 keeps the adhesive 28 more securely fastened to the skin 102. This may in turn be covered by a bulkier protective covering of various materials.

The method to operate the tissue wound device 2, the user removes the adhesive cover 27 from the back of the anchor base 4 and the receiving base 6. The adhesive 28 connects the anchor base 4 and the receiving base 6 to the skin 102. Specifically, the anchor base 4 is placed next to the edge of the tissue wound 100. The receiving base 6 is placed on the opposing side of the tissue wound 100. The tip 24 is inserted into the slide port 30 located on the receiving base 6. However, the tip 24 may be inserted during the manufacturing process.

The key 50 is then inserted onto the boss 12 located on the receiving base 6. As the user turns the key 50, rotational motion of the pinion 54 is converted into a linear motion of the tie strip 8 and the anchor base 4 in such a way that the distance between the anchor base 4 and the receiving base 6 decreases. An alternative to the key 50, is the utilization of the lever 70.

As the space between the anchor base 4 and the receiving base 6 decreases, the skin 102 is pulled together and closes the tissue wound 100. The teeth 16 and the pawl 15 maintain the distance between the anchor base 4 and the receiving base 6. This system allows the user to carefully make incremental movements of the skin 102. Once the wound is appropriately closed, the lock 60 may be utilized to prevent any movement.

While a preferred embodiment of the invention of the device has been shown and described herein, it should, however, be understood that the description above contains many specifics that should not be construed as limiting the scope of the invention. Thus, the scope of the embodiment should be determined by the appended claims and their legal equivalents thereof, rather than by the examples given.

What is claimed is:

1. A tissue closing device comprising:
   (a) an anchor base and a receiving base; the bottom of the anchor base and the receiving base having an adhesive; the receiving base having a receiving body;
   (b) a tie strip having a plurality of teeth, and a rack; wherein the tie strip connects with the anchor base;
   (c) the receiving body having a slide port and a pawl extending into the slide port; the slide port is for receiving the tie strip; the pawl is adapted to engage with the teeth on the tie strip for preventing movement of said base portion in a release direction;
   (d) a key having a pinion; wherein the key releasably connects with the receiving body; the pinion corresponds with the rack on the tie strip;
   wherein rotational motion to the key causes the rack on the tie strip to move relative to the pinion, thereby translating the rotational motion of the pinion into linear motion of the tie strip and the anchor base, such that the distance between the anchor base and the receiving base decreases; the teeth and the pawl maintains the distance between the anchor base and receiving base.

2. The invention as recited in claim 1, wherein said receiving base having a boss; said key having an orifice; wherein, the orifice releasably connects with the boss on the receiving body.

3. The invention as recited in claim 1, wherein said receiving body having a latch and catch; the latch having a lock and a lock clasp; wherein, the lock clasp engages with the catch to prevent movement of said tie strip.

4. The invention as recited in claim 1, wherein a pad is located between said anchor base and said adhesive; and the pad is located between said receiving base and said adhesive.

5. The invention as recited in claim 4, wherein in the pad is made of a flexible material.

6. The invention as recited in claim 1, wherein a coupler connects two or more said tissue closing device forming an array.

7. The invention as claimed in claim 6, wherein said coupler is made of a flexible material.

8. The invention as claimed in claim 6, wherein more than one coupler connects each said tissue closing device.

9. The invention as claimed in claim 1, wherein said key has a shaft for extending said handle above said receiving base.

10. The invention as claimed in claim 1, wherein said tissue closing device having an arc shape.

11. A method for closing a tissue wound utilizing a sutureless device:
   A) providing a tissue closing device which
   (i) an anchor base and a receiving base; the bottom of the anchor base and the receiving base having an adhesive; the receiving base having a receiving body;
   (ii) a tie strip having a plurality of teeth, and a rack; wherein the tie strip connects with the anchor base;
   (iii) the receiving body having a slide port and a pawl extending into the slide port; the slide port is for receiving the tie strip; the pawl is adapted to engage with the teeth on the tie strip for preventing movement of said base portion in a release direction;

(iv) a key having a pinion; wherein the key releasably connects with the receiving body; the pinion corresponds with the rack on the tie strip;

wherein rotational motion to the key causes the rack on the tie strip to move relative to the pinion, thereby translating the rotational motion of the pinion into linear motion of the tie strip and the anchor base, such that the distance between the anchor base and the receiving base decreases; the teeth and the pawl maintains the distance between the anchor base and receiving base;

B) The anchor base is attached near the edge of a tissue wound; the receiving base is attached on the opposite side near the edge of the tissue wound;

C) connecting the key and the receiving base;

D) rotating the key, wherein the pinion causes the rack, the tie strip and the anchor base to move, wherein the distance between the anchor base and the receiving base is decreased and the tissue wound is closed;

E) the key is removed.

12. The method as claimed in claim 11, wherein a bandage is placed over said tissue closing device.

13. The method as claim in claim 11, wherein said receiving body having a latch and catch; the latch having a lock and a lock clasp; wherein, the lock clasp engages with the catch to prevent movement of said tie strip; wherein, the user engages the lock to prevent movement on said tie strip.

* * * * *